United States Patent
Chu

(10) Patent No.: US 9,820,730 B2
(45) Date of Patent: Nov. 21, 2017

(54) TENSION ADAPTER FOR MEDICAL DEVICE

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 793 days.

(21) Appl. No.: 12/970,381

(22) Filed: Dec. 16, 2010

(65) Prior Publication Data

US 2011/0190792 A1 Aug. 4, 2011

Related U.S. Application Data

(60) Provisional application No. 61/301,422, filed on Feb. 4, 2010.

(51) Int. Cl.
*A61B 17/04* (2006.01)

(52) U.S. Cl.
CPC .......... *A61B 17/04* (2013.01); *A61B 17/0483* (2013.01); *A61B 17/0487* (2013.01)

(58) Field of Classification Search
CPC . A61B 17/04; A61B 17/0482; A61B 17/0483; A61B 17/0487; A61B 2017/0438; A61B 2017/0445; A61B 2017/0404; A61B 2017/0406
USPC ............................. 606/144, 148, 232; 600/37
See application file for complete search history.

(56) References Cited

U.S. PATENT DOCUMENTS

| | | | | |
|---|---|---|---|---|
| 3,254,651 | A | * | 6/1966 | Collito .......................... 606/153 |
| 4,702,250 | A | * | 10/1987 | Ovil et al. .................... 606/148 |
| 5,693,060 | A | * | 12/1997 | Martin .......................... 606/148 |
| 5,741,277 | A | | 4/1998 | Gordon et al. |
| 5,797,928 | A | * | 8/1998 | Kogasaka ..................... 606/144 |
| 5,797,929 | A | * | 8/1998 | Andreas et al. .............. 606/148 |
| 6,015,428 | A | * | 1/2000 | Pagedas ........................ 606/232 |
| 6,346,111 | B1 | | 2/2002 | Gordon et al. |
| 6,679,896 | B2 | * | 1/2004 | Gellman et al. .............. 606/148 |
| 6,817,634 | B2 | * | 11/2004 | Champion ..................... 289/17 |
| 6,936,054 | B2 | | 8/2005 | Chu |
| 7,033,370 | B2 | | 4/2006 | Gordon et al. |
| 7,041,111 | B2 | | 5/2006 | Chu |
| 7,060,077 | B2 | | 6/2006 | Gordon et al. |
| 7,122,039 | B2 | | 10/2006 | Chu |
| 7,232,447 | B2 | | 6/2007 | Gellman et al. |
| 7,615,061 | B2 | * | 11/2009 | White et al. .................. 606/148 |

(Continued)

*Primary Examiner* — Alexander Orkin
(74) *Attorney, Agent, or Firm* — Brake Hughes Bellermann LLP

(57) ABSTRACT

Devices and methods are described herein directed to an adaptor for use with a medical device used to suture tissue within a patient's body and/or for delivering and/or securing another medical device within a patient's body. In one embodiment, an apparatus to aid in the placement of a suture at a location within a body of a patient using a medical device includes a body and a coupler configured to couple the body to the medical device. The apparatus further includes a suture mounting portion disposed on the body that defines a suture slit configured to laterally receive therethrough a portion of a suture coupled to the medical device and to apply a frictional force to the suture to resist movement of the suture longitudinally therethrough. A magnitude of the frictional force being less than a longitudinal force applied to the suture by actuation of the medical device.

15 Claims, 13 Drawing Sheets

(56) References Cited

U.S. PATENT DOCUMENTS

| | | |
|---|---|---|
| 8,012,174 B2* | 9/2011 | ElAttrache et al. .......... 606/232 |
| 2003/0055439 A1* | 3/2003 | Koseki ........................ 606/148 |
| 2003/0093091 A1* | 5/2003 | Paolitto et al. .............. 606/139 |
| 2004/0181243 A1 | 9/2004 | Chu et al. |
| 2004/0254593 A1* | 12/2004 | Fallin et al. ................. 606/148 |
| 2005/0065535 A1* | 3/2005 | Morris et al. ................ 606/148 |
| 2006/0095054 A1* | 5/2006 | Zannis et al. ................ 606/148 |
| 2006/0195121 A1 | 8/2006 | Chu |
| 2006/0206119 A1 | 9/2006 | Chu |
| 2007/0060929 A1* | 3/2007 | Onishi et al. ................ 606/139 |
| 2007/0173864 A1 | 7/2007 | Chu |
| 2007/0203508 A1* | 8/2007 | White et al. ................. 606/148 |
| 2008/0109015 A1 | 5/2008 | Chu et al. |
| 2009/0171139 A1 | 7/2009 | Chu |
| 2009/0171140 A1 | 7/2009 | Chu |
| 2009/0171142 A1 | 7/2009 | Chu |
| 2009/0171143 A1 | 7/2009 | Chu et al. |
| 2009/0248028 A1* | 10/2009 | Alexander .................... 606/103 |
| 2010/0106170 A1* | 4/2010 | Eckerdal et al. ............. 606/148 |
| 2010/0191261 A1* | 7/2010 | Carter et al. ................ 606/150 |

* cited by examiner

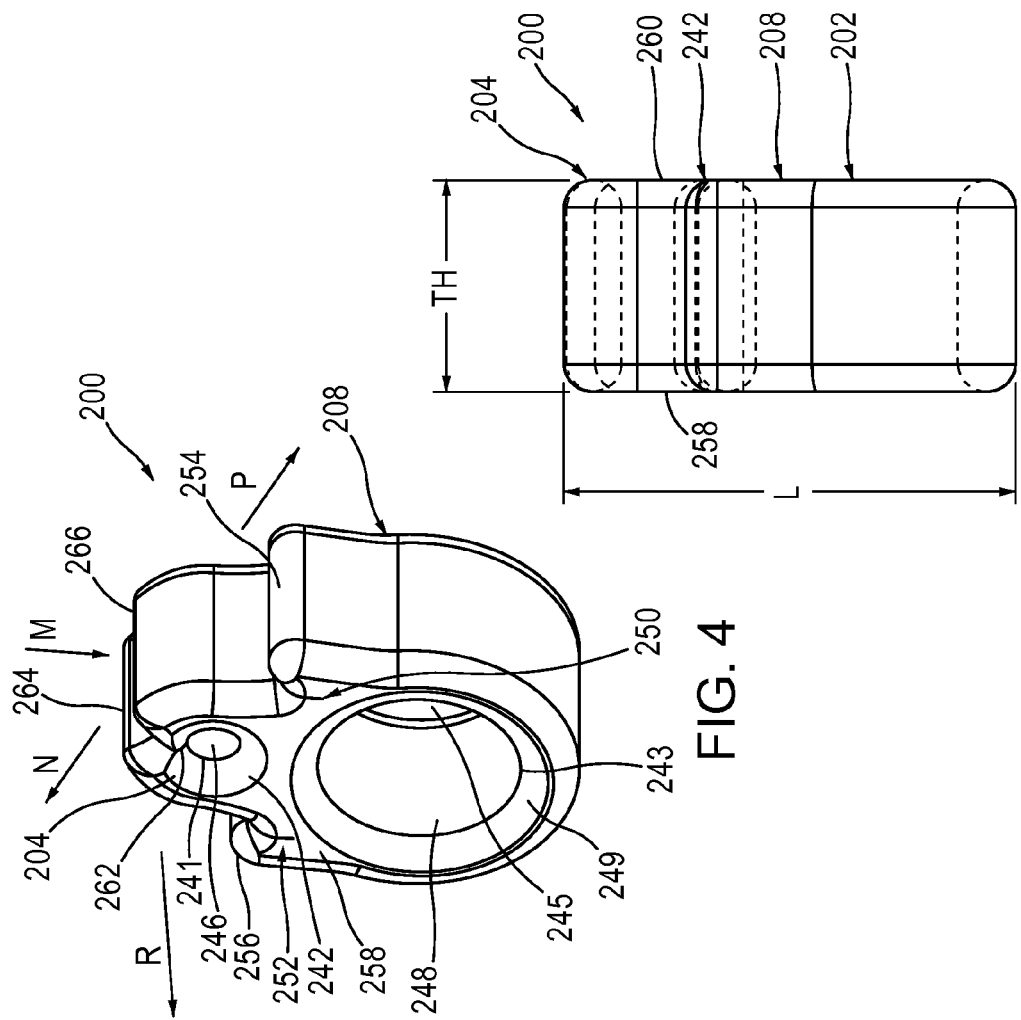
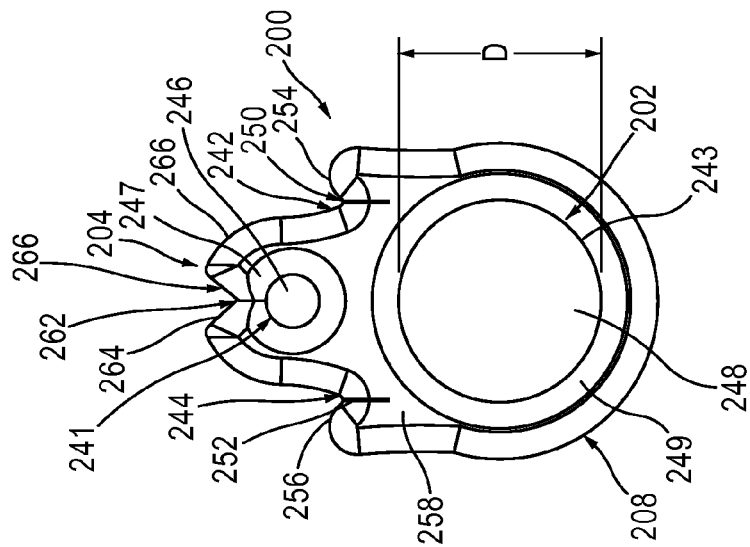
FIG. 4
FIG. 5
FIG. 6

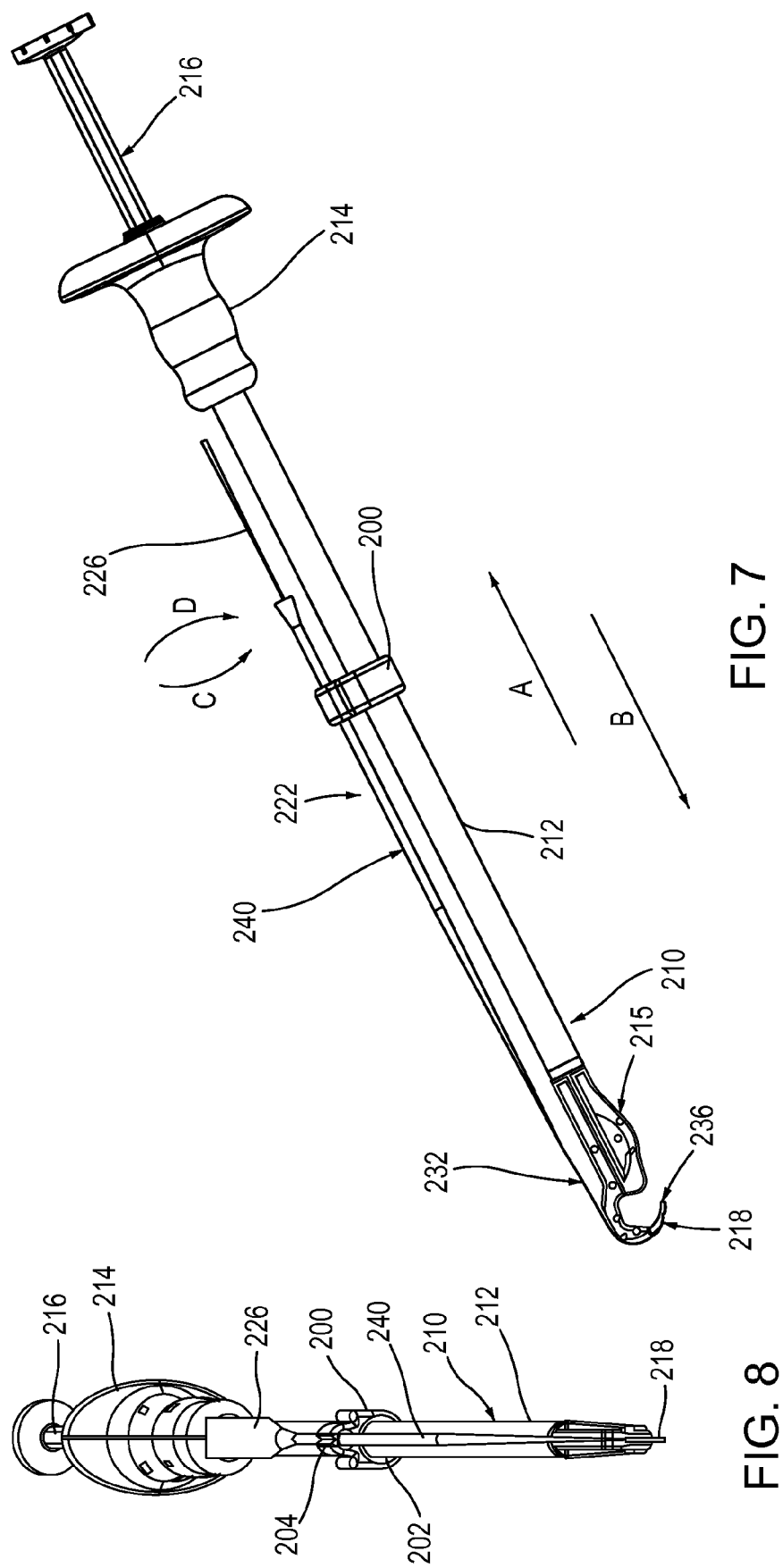

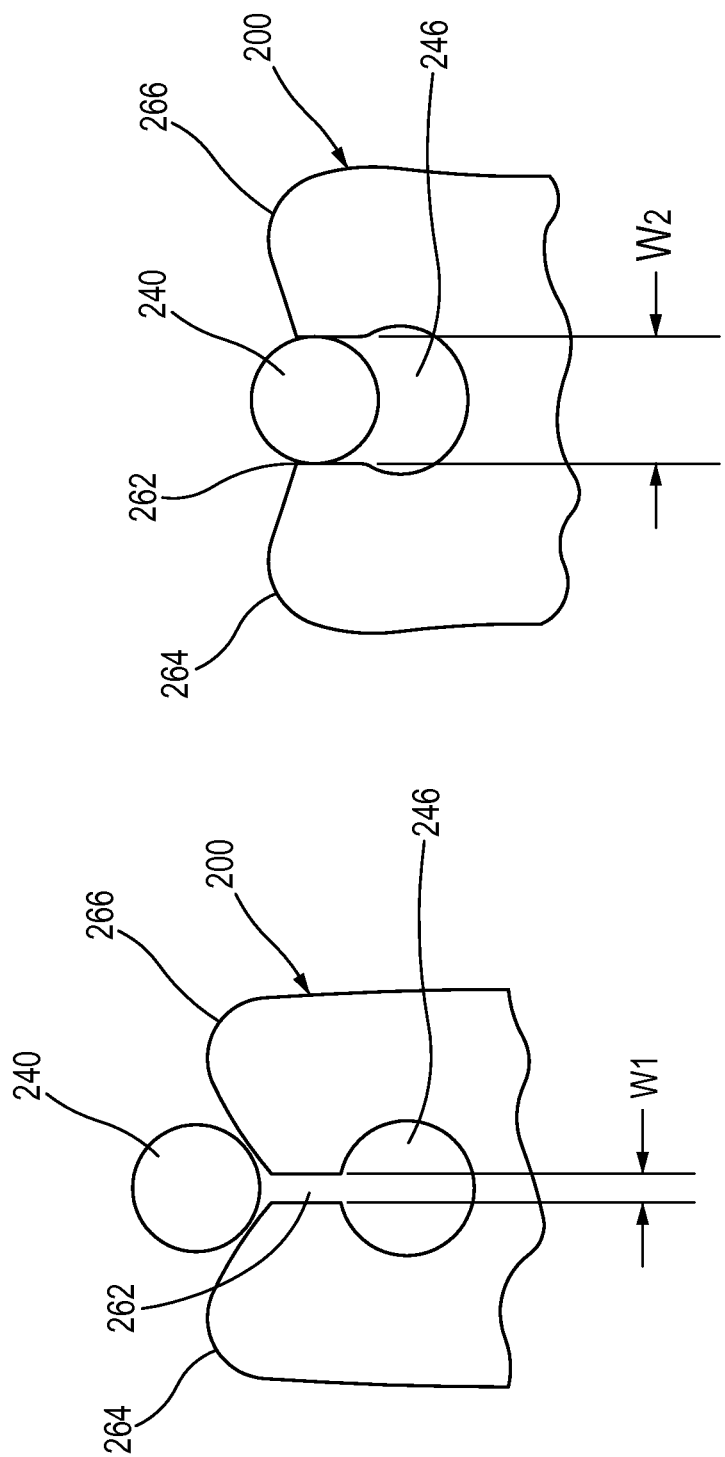

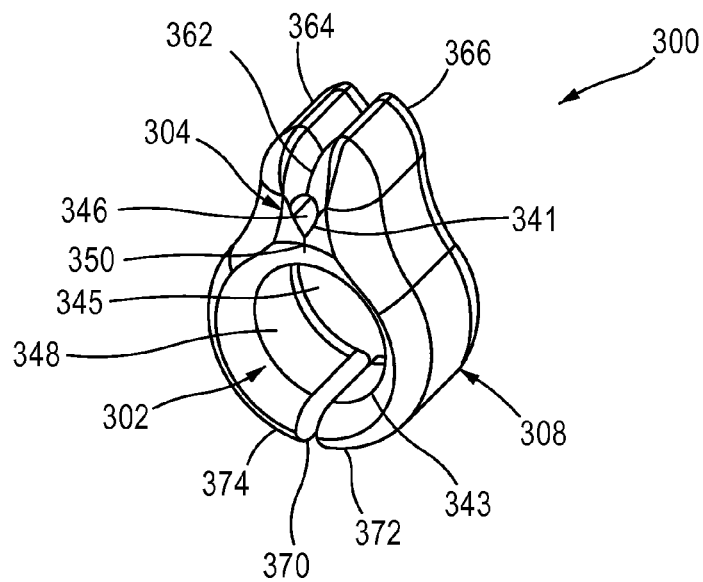
FIG. 13
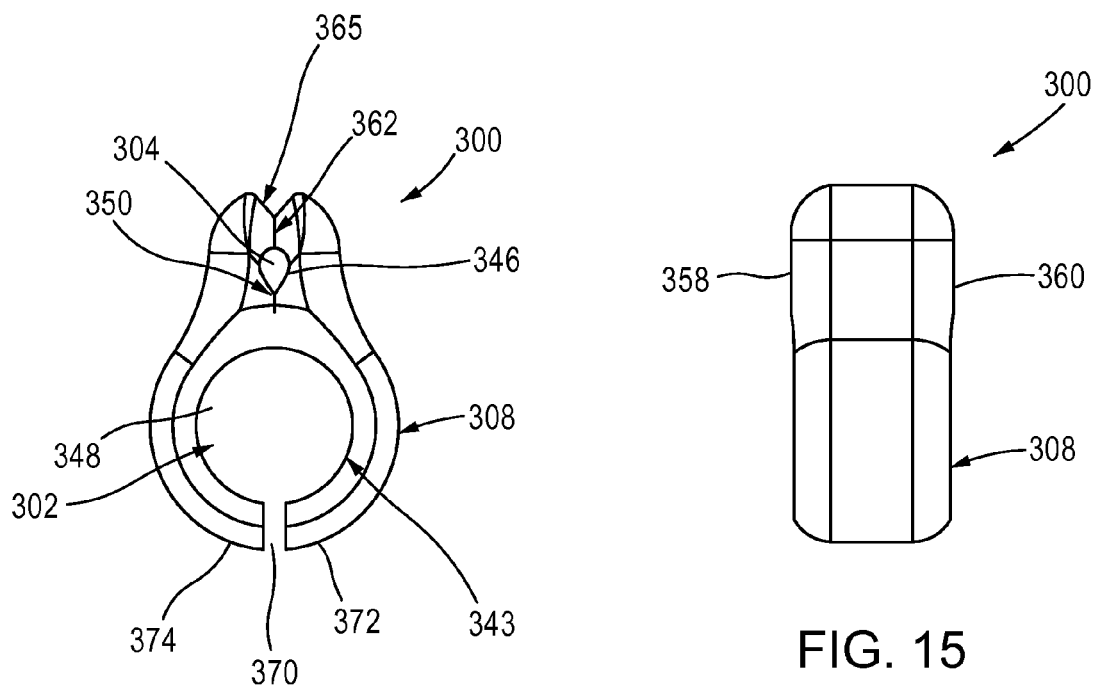
FIG. 14
FIG. 15

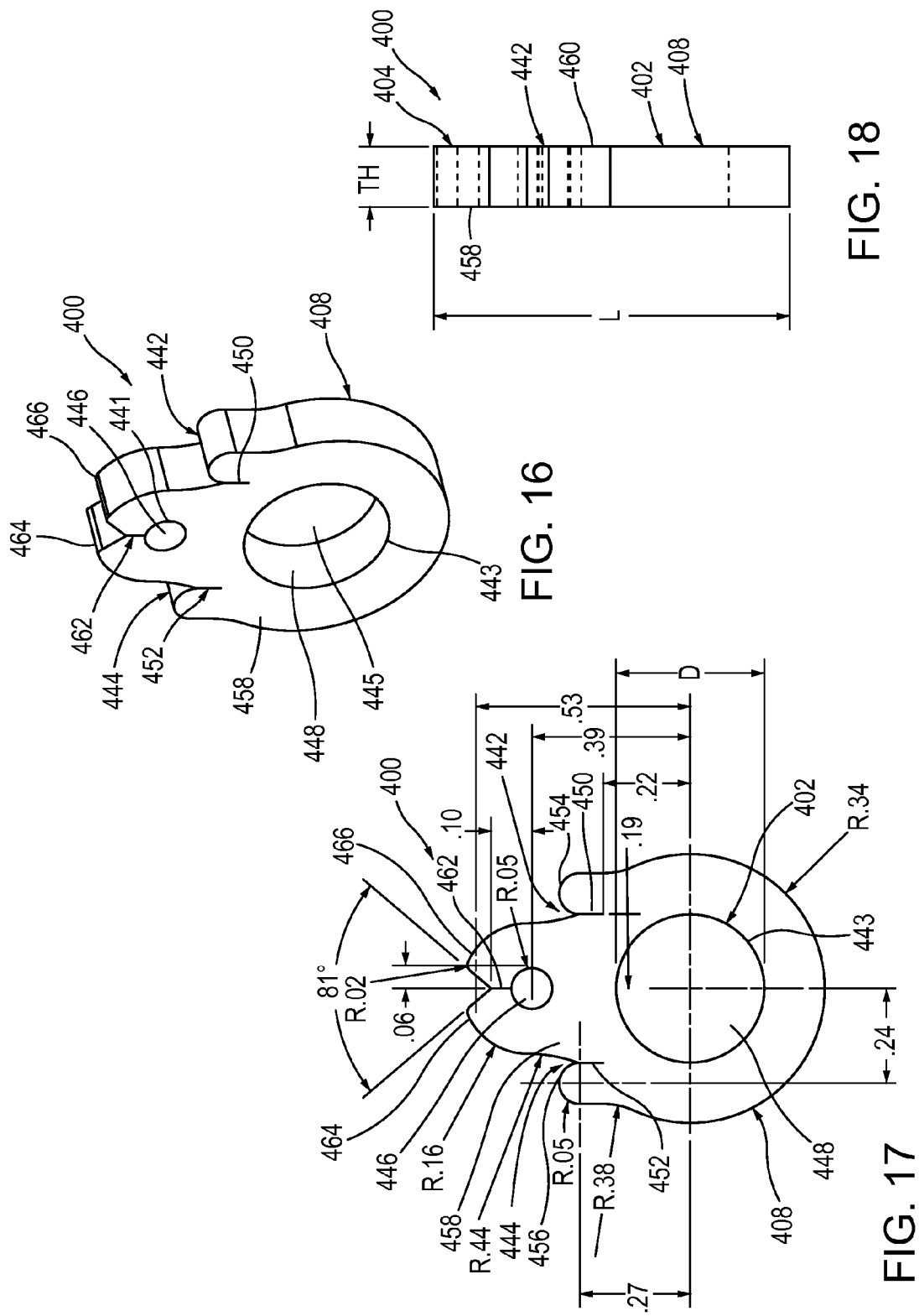

TENSION ADAPTER FOR MEDICAL DEVICE

RELATED APPLICATION

This application claims priority to and the benefit of U.S. Provisional Patent Application Ser. No. 61/301,422, filed on Feb. 4, 2010, entitled, "Tension Adaptor for Medical Device," which is incorporated herein by reference in its entirety.

BACKGROUND

The disclosed invention relates generally to medical devices and more particularly to methods and devices for delivering and securing implants and/or sutures to a desired location within a body of a patient.

Many medical procedures require suturing of body tissue and or suturing or securing an implant or other medical device within an interior region of a patient's body. Some surgical instruments used to suture body tissue and/or to secure an implant within a patient are limited by the manner in which they access the areas of the patent's body in need of repair. Suturing can be a delicate and time-consuming aspect of a medical procedure. Some medical procedures that may require suturing and/or securing of a medical implant include procedures to treat various female pelvic dysfunctions, including procedures to treat urinary incontinence, and correcting various prolapse conditions such as uterine prolapse, cystoceles, rectoceles, and vaginal vault prolapse.

Treatment for such dysfunctions has included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Various complications can occur during a procedure to deliver and secure a pelvic implant due to, for example, space constraints for performing the implantation procedure. Often, implants can become damaged during delivery due to the type of delivery device and/or the type of implant, or due to excessive handling of the implant during the implant procedure.

Some suturing and/or delivery devices used in such procedures may require that the user have a certain level of dexterity and organization skills. For example, if one hand (e.g., forefinger) is used to palpate the tissue, and the other hand is used for activation of the suturing device and tensioning if needed, operation of the device can pose some difficulty. Over tensioning or non-release of the suture or device can lead to breakage of the suture or device, which can increase the time required to perform the procedure. Thus, it would be desirable to provide improved delivery processes associated with such procedures to improve and make easier the handling of such suturing and delivery devices.

SUMMARY OF THE INVENTION

In one embodiment, an apparatus to aid in the placement of a suture at a location within a body of a patient using a medical device includes a body and a coupler configured to couple the body to the medical device. The apparatus further includes a suture mounting portion disposed on the body that defines a suture slit configured to laterally receive therethrough a portion of a suture coupled to the medical device and to apply a frictional force to the suture to resist movement of the suture longitudinally therethrough. A magnitude of the frictional force being less than a longitudinal force applied to the suture by actuation of the medical device.

BRIEF DESCRIPTION OF THE DRAWINGS

FIG. 4 is a perspective view of an adaptor according to an embodiment.

FIG. 5 is a front view of the adaptor of FIG. 4.

FIG. 6 is a side view of the adaptor of FIG. 4.

FIG. 7 is a side view illustrating the adaptor of FIG. 4 coupled to the medical device of FIG. 2 and the dilator assembly of FIG. 3.

FIG. 8 is a top view of the adaptor, medical device and dilator assembly of FIG. 7.

FIG. 9A is a front view of a portion of the adaptor of FIG. 4 and a portion of the dilator assembly of FIG. 3 shown with the adaptor in a first configuration.

FIG. 9B is a front view of the portion of the adaptor and the portion of the dilator assembly of FIG. 9A shown with the adaptor in a second configuration.

FIG. 13 is a perspective view of an adaptor according to another embodiment.

FIG. 14 is a front view of the adaptor of FIG. 13.

FIG. 15 is a side view of the adaptor of FIG. 13.

FIG. 16 is a perspective view of an adaptor according to another embodiment.

FIG. 17 is a front view of the adaptor of FIG. 16.

FIG. 18 is a side view of the adaptor of FIG. 16.

DETAILED DESCRIPTION

The devices and methods described herein are generally directed to an adaptor for use with a medical device used to suture tissue within a patient's body and/or for delivering and/or securing another medical device (such as a stent or implant) within a patient's body. For example, a medical device such as a suturing device can be used to place sutures within tissue of a body of a patient. A suturing device can also be used to secure an implant to a body tissue. A suturing device can also be used to deliver an implant that can secure itself to tissue in an interior region of a patient's body. For example, an implant can include a portion that can include one or more tanged portion and/or one or more detanged portion. The terms "tanged" or "tangs" as used herein mean roughened or jagged edges or areas, such as can result from cutting a woven or knit mesh material. The tanged portion can be used, for example, to anchor or secure the implant to tissue.

An adaptor as described herein can be used with a variety of different types of medical devices, such as, for example, various suturing and/or delivery devices. Various configurations of a suturing or delivery device are described herein which can be used to place a suture or implant within a patient's body such as in a lumen, passage, cavity or other area within a patient's body.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve or dilator assembly as described herein refers to the end or portion of the device that is first inserted into a body of a patient during a medical procedure. The proximal end or portion is the end or portion of the device that is inserted into a body of the patient after the distal end or portion.

Figure 1:
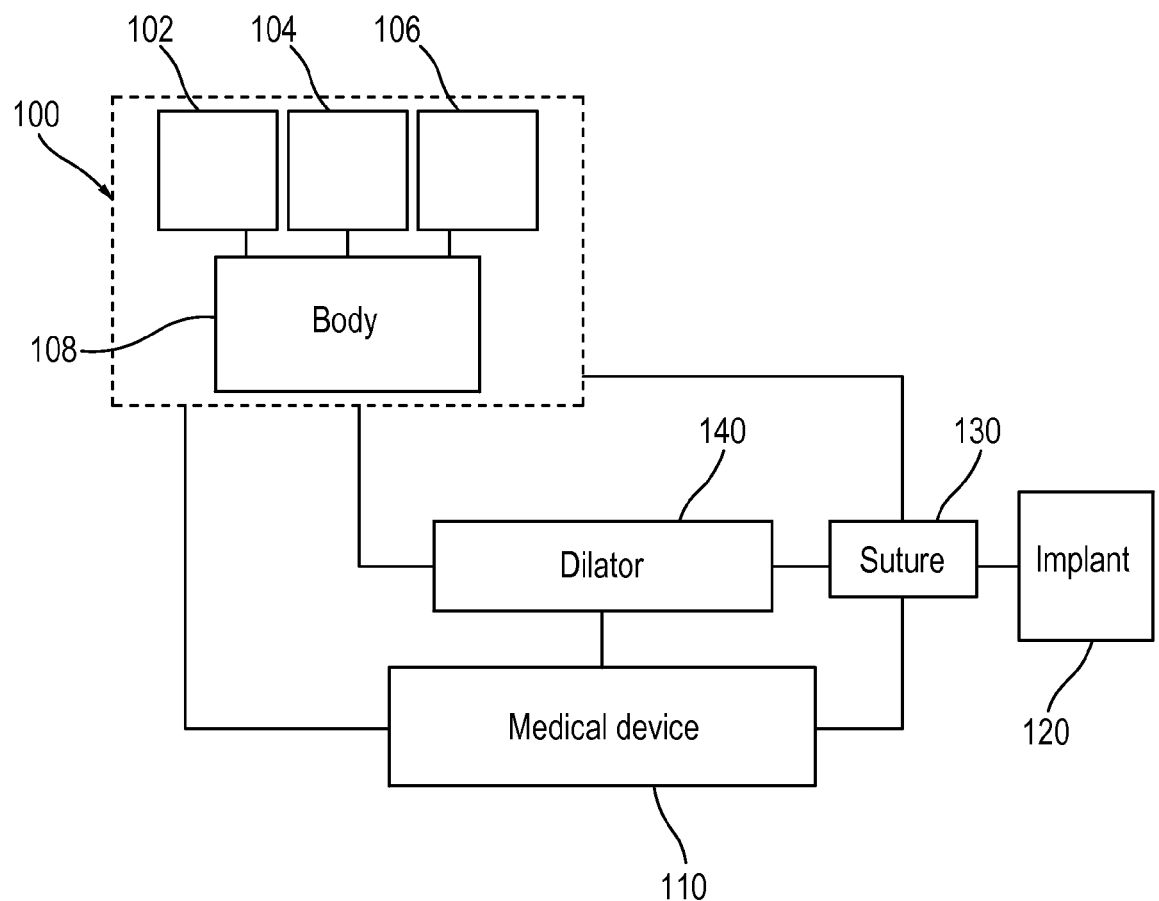
FIG. 1 is a schematic illustration of an adaptor according to an embodiment shown with a schematic illustration of a medical device, an implant and a suture.
Figure 2:
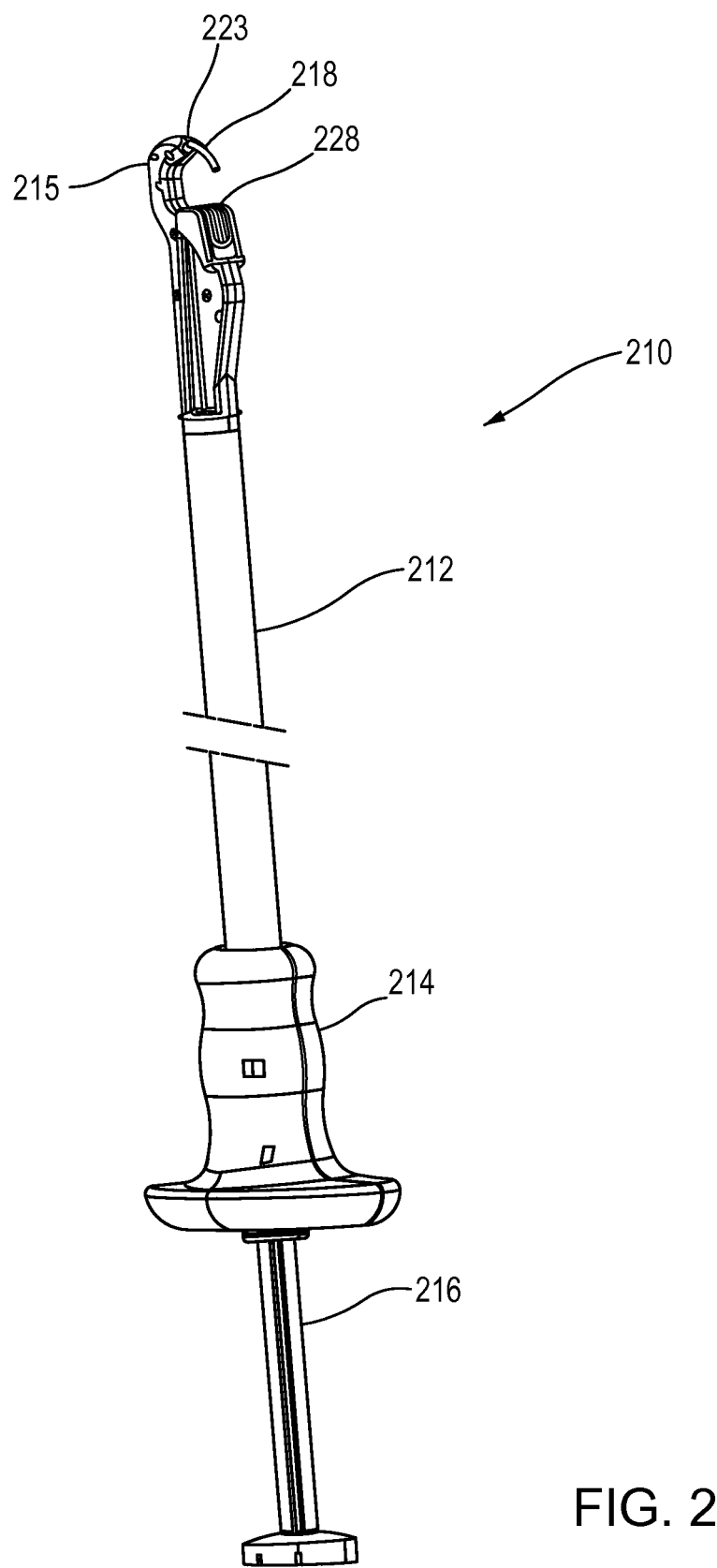
FIG. 2 is a side view of an exemplary medical device with which the subject adaptor may be used.

FIG. 1 is a schematic illustration of various components, including an adaptor according to an embodiment. Various medical procedures benefit from the use of a medical device 110, such as suturing device or a delivery device, to for example, deliver an implant 120 to an interior location within a patient's body, and/or to place sutures 130 in tissue within a patient's body. An example suturing/delivery device is sold under the name CAPIO by Boston Scientific Corporation. There are a variety of different types of CAPIO device that are available for use in various different procedures. In some embodiments, a CAPIO device can be used to deliver self-affixing straps of an implant to a pelvic region of a patient, or to place sutures, as described in U.S. Patent Pub. No. 2009/0171142 and U.S. Patent Pub. No, 2009/0171143, each of the disclosures of which is hereby incorporated by reference in its entirety. One example embodiment of a CAPIO device is shown in FIG. 2 (described in more detail below). The details and function of various types of suturing and/or delivery devices are described, for example, in U.S. Pat. Nos. 7,041,111; 7,232,447; 5,741,277; 6,936,054; 7,033,370; 7,122,039; 6,346,111; 7,060,077 and U.S. Patent Pub. Nos. 2007/0173864; 2008/0109015; 2004/0181243; 2006/0195121 and 2006/0206119, each of the disclosures of which is hereby incorporated by reference in its entirety.

An implant 120 as described herein can be a variety of different configurations, shapes and sizes. According to some embodiments, an implant can be a pelvic implant that can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include a single vaginal incision, such as an anterior vaginal incision and/or an anterior vaginal incision and a posterior vaginal incision. In some embodiments, a procedure may include an exterior incision.

Figure 3:
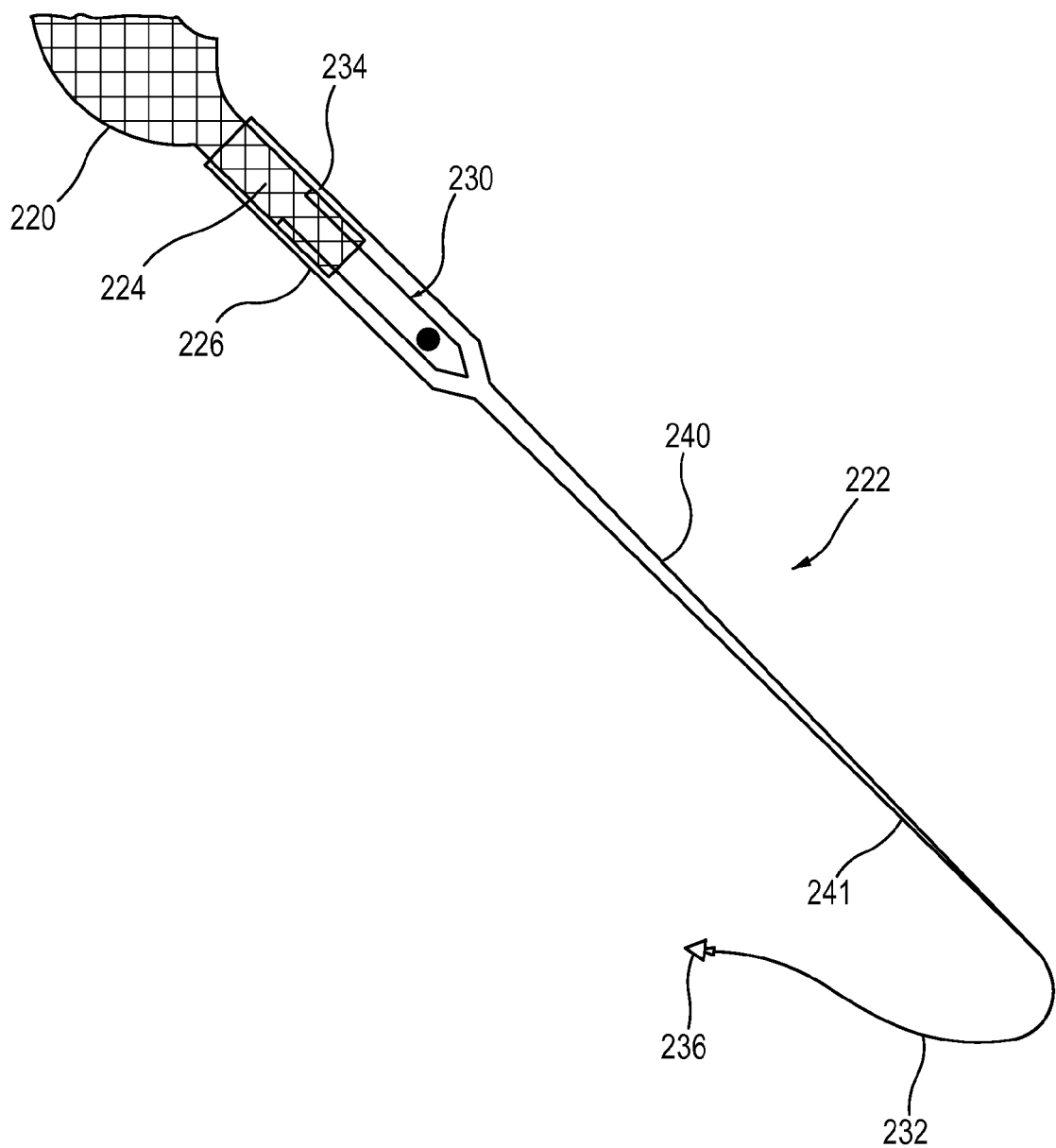
FIG. 3 is top view of a portion of an exemplary implant coupled to a dilator assembly with which the subject adaptor may be used.

In some embodiments, an implant is coupled to a dilator assembly 140 that is used to introduce a portion of the implant through tissue. For example, a strap of an implant can be pulled through a tissue with the help of a dilator assembly, and fastened thereto with self-affixing mesh or with sutures. FIG. 3 illustrates one example embodiment of a portion of an implant with a dilator assembly coupled thereto. Other example implants are described in U.S. Patent Pub. No. 2009/0171142 and U.S. Patent Pub. No, 2009/0171143 incorporated by reference above.

In some uses of a medical device 110, the medical practitioner may use one hand to palpate tissue and the other hand to activate the medical device (e.g., activate the medical device to place a suture in tissue). For example, a medical device 110 can be used to deliver a strap of an implant 120 coupled to a dilator assembly that includes a suture coupled to a dilator. In such a procedure, the user may need to maintain tension on the suture or dilator during the manipulation or positioning of the medical device 110 to ensure that the dart (e.g., needle) coupled to the suture is maintained within a carrier of the device. Once the device is fired or activated, tension on the suture or dilator needs to be released to advance the dart out of the carrier and into the desired location. Over tensioning or non-release of the suture or dilator can lead to breakage of the suture or the medical device 110, which can prolong and/or complicate the procedure. To help organize and maintain the tension on the suture and/or dilator during the procedure, an adaptor 100 can be coupled to the medical device 110 and used to hold the suture in tension and maintain the needle in the carrier of the medical device 110.

The adaptor 100 includes a body 108 that can include a coupling portion 102 (also referred to as "coupler") used to couple the adaptor 100 to a medical device 110. The coupling portion 102 can be a separate component coupled to the body 108, or can be formed integrally or monolithically with the body 108. In some embodiments, the coupling portion 102 can couple the adaptor 100 to a shaft or elongate portion of the medical device 110. For example, in some embodiments, the coupling portion 102 of the adaptor 100 includes a lumen (also referred to as medical device lumen) through which the medical device 110 can be slidably received. In some embodiments, such a lumen is defined by the body 108. The coupling portion 102 of the adaptor 100 can alternatively include other known coupling methods, such as, for example, clips, clamps, crimps, fasteners, etc.

The adaptor 100 can be coupled to the medical device 110 during a manufacturing/assembly process of the medical device 110 or coupled later by the user (e.g., medical practitioner) when a medical procedure is to be performed. In some embodiments, an adaptor 100 can be permanently or fixedly attached to a medical device 110, such as with an adhesive. Thus, an adapter 100 can be provided as a separate component to be coupled to one or more types of medical devices 110, or can be incorporated or provided with a particular medical device 110. The adaptor 100 and a medical device 110 can also be provided in a kit, as described in more detail below with reference to FIG. 18.

The medical device lumen of the adaptor 100 can be sized such that the medical device 110 can be received therethrough while at the same time being sized such that compression and/or friction force applied by the adaptor 100 secures or maintains the adaptor 100 on the medical device 110. In some embodiments, the medical device lumen of the adaptor 100 can be slightly smaller than the outer perimeter or outer diameter of the medical device 110. In some embodiments, the surface of the inner walls of the adaptor 100 that define the lumen can be roughened or otherwise configured to provide a friction fit between the medical device 110 and the adaptor 100.

In some embodiments, the coupling portion 102 of the adaptor 100 can also include a slot (not shown in FIG. 1) in fluid communication with the medical device lumen. In such an embodiment, the medical device 110 can be moved through the slot and into the medical device lumen. For example, the adaptor 100 can be formed with a resilient or elastic material such that the adaptor 100 can deform to allow the slot to expand from a first width to a larger second width as the medical device 110 is moved through the slot and into the medical device lumen of the adaptor 100. After the medical device 110 is disposed within the lumen of the adaptor 100, the adaptor 100 can deform back to its original shape (or substantially thereto) with the slot at its smaller first width. The first width can be sufficiently small so as to prevent the medical device 110 from coming out of the lumen of the adaptor 100 in the absence of a specified amount of force being applied to remove the medical device 110 from the medical device lumen.

The adaptor 100 can also include one or more dilator holding portions 104. As with the coupling portion 102, the dilator holding portion 104 can be formed integrally or monolithically with the body 108 or can be a separate component couplable to the body 108. In some embodiments, the dilator holding portion 104 includes a lumen (also referred to as "dilator lumen") through which a dilator 140 can be inserted or placed. In some embodiments, the dilator lumen can be defined by the body 108. As with the lumen for the medical device 110, the dilator lumen can be sized such that the dilator 140 can be received therethrough while at the same time being sized such that a compression and/or friction force applied by the adaptor 100 secures or maintains the dilator 140 coupled to the adaptor 100. In some embodiments, the dilator lumen of the adaptor can be slightly smaller that the outer perimeter or outer diameter of the dilator 140.

In some embodiments, a compression force applied by the adaptor 100 on the dilator 140 can produce a friction force of, for example, less than 1 pound-force. In some embodiments, the surface of the inner walls of the adaptor 100 that define the dilator lumen can be roughened or otherwise configured to increase the coefficient of friction between the dilator 140 and the adaptor 100. The applied friction force is sufficient to hold the dilator 140 within the dilator lumen. The force can be overcome, for example, by a force applied by actuation of the medical device 110 as described in more detail below.

The dilator holding portion 104 of the adaptor 100 can also include a dilator slot (not shown in FIG. 1) in fluid communication with the dilator lumen such that the dilator 140 can be moved through the dilator slot and into the dilator lumen. The dilator slot can be a variety of different shapes, such as round, square, diamond, oval, etc. In addition, an adaptor 100 can be formed with more than one dilator lumen and/or dilator slot. Each dilator lumen and/or slot can be shaped and/or sized the same or differently to accommodate different dilators or other devices. For example, an adaptor can include multiple dilator lumens so that it can be used to organize the delivery of multiple straps of an implant. In some embodiments, an adaptor 100 may not include a dilator lumen and/or slot.

As discussed above, the adaptor 100 can be formed with a resilient or elastic material such that it can deform to allow the dilator slot to expand from a first width to a larger second width as the dilator 140 is moved through the slot and into the dilator lumen of the adaptor 100. After the dilator 140 is disposed within the lumen of the adaptor 100, the adaptor 100 can recover back to its original shape (or substantially thereto) with the dilator slot at its smaller first width. The first width can be sufficiently small so as to prevent the dilator 140 from coming out of the lumen of the adaptor 100 in the absence of a predetermined amount of force being applied to remove the dilator 140 from the dilator lumen. The dilator mounting portion 104 can also include a lead-in portion to help ease the entry of a dilator 140 through the dilator slot. For example, the lead-in portion can be defined by a chamfer or with a radiused portion as described in more detail with reference to specific embodiments below.

The adaptor 100 can also include one or more suture mounting portions 106 that can receive and secure a portion of a suture 130 to the adaptor 100. The suture mounting portion 106 can be formed integrally or monolithically with the body 108, or can be a separate component couplable to the body 108. In some embodiments, the suture mounting portion 106 can include a suture slit (not shown in FIG. 1) in which the suture 130 can be held. The suture slit can be formed, for example, by cutting with a razor or other sharp instrument or by molding into the material of the adaptor 100. Similar to the dilator lumen, the suture slit of the adaptor 100 can provide a compression force and/or friction force on the suture 130 when it is placed within the suture slit and maintain a tension on the suture 130 during a medical procedure. The suture slit arc size can be narrower than a diameter of the suture to provide a friction and/or compression between the suture slit and the suture 130. In some embodiments, the adaptor 100 can provide, for example, a compression force on the suture 130 within the suture slit of less than 1 pound-force. As with the dilator lumen, the friction and/or compression on the suture can be overcome when the medical device is actuated. The suture mounting portion 106 can also include a lead-in region to help insert a suture 130 within the suture slit. For example, the lead-in portion can be defined by a chamfer or with a radiused portion as described in more detail with reference to specific embodiments below. A suture 130 can be moved through the lead-in portion and laterally moved into the slit.

As discussed above, the adaptor 100 can be formed with, for example, an elastic or rubber material. For example, in some embodiments, the adaptor 100 can be formed with a medical grade silicone, such as one with a hardness of about 50 durometer. In some embodiments, the adaptor 100 can be formed with a medical grade silicone, such as one with a hardness of about 70 durometer. An elastic or rubber material can allow the adaptor 100 to deform as described above and recover back to a relaxed state to cause compression against the suture or dilator (or other device) coupled to the adaptor 100. The adaptor 100 can be formed by various methods including, for example, molding or die cut. As described below with reference to specific embodiments, the adaptor 110 can prevent over tensioning of the suture, dilator and/or device, and therefore, can free up the activation hand of the user. Thus, the operation of the medical device 110 can be made simpler.

Having described above various general principles, several exemplary embodiments of these concepts are now described. These embodiments are only examples, and many other configurations of an implant, sleeve assembly, or dilator assembly, etc., are contemplated.

FIG. 2 illustrates an example medical device to which an adaptor as described herein can be coupled and used therewith. As shown in FIG. 2, a medical device 210 includes an elongate shaft 212, a handle 214, an actuator 216 operatively coupled to the handle 214 and a head portion 215. The head portion 215 includes a needle carrier 218 and a catch 228. The medical device 210 can function in the same manner as a CAPIO device mentioned above and the various suturing and delivery devices described in any of the references incorporated by reference above. The medical device 210 can be used to place a suture in body tissue and/or to deliver an implant to a location within a body and/or to secure the implant to a tissue. For example, the medical device 210 can be used to deliver and securer a pelvic implant to a desired location within a pelvic region of a patient's body. FIG. 3 shows a portion of a pelvic implant 220 coupled to a dilator assembly 222. The below description of the use of an adaptor 200 is described with reference to the example medical device 210 and implant 220.

The implant 220 includes one or more straps 224 (one shown) coupled to a dilator assembly 222. The dilator assembly 222 includes a sleeve 226 coupled to a dilator 240. The dilator 240 is coupled to a suture 230 that can extend through a lumen of the dilator 240 such that a distal portion 232 of the suture 230 extends from a distal end 241 of the dilator 240. A proximal portion 234 of the suture 230 can be coupled to the sleeve 226 and/or the strap 224 of the implant 220. A needle 236 is coupled to a distal end of the suture 230. The dilator assembly 222 is only one example of a dilator assembly that can be used with an adaptor as described herein. For example, other dilators that can be used are described in U.S. Patent Pub. Nos. 2009/0171139 and 2009/0171140, each of the disclosures of which is hereby incorporated by reference in its entirety.

To use the medical device 210 to deliver the strap 224 of the implant 220 through a tissue in a body of a patient, the needle 236 is loaded into the carrier 218 (shown partially extended in FIG. 2) of the medical device 210. The needle 236 is held within the carrier 218 with a slight friction fit. The medical device 210 can then be used to pass the needle 236 and the strap 224 (with the sleeve 226 attached thereto) through a pelvic tissue. Specifically, the carrier 218 of the medical device 210 is positioned adjacent a selected tissue site and the medical device 210 is actuated by pushing the actuator 216, which in turn pushes a spring-loaded rod (not shown), which pushes the needle carrier 218 out of a needle exit port 223 (see FIG. 2). The user continues to push the actuator 216 until the needle 236 pierces through the tissue and is caught or retrieved by the catch 228. The medical device 210 can then be removed from the patient's body and the sleeve 226 pulled through the tissue. For example, the user can pull the distal portion 232 of the suture or the dilator 240 through the tissue such that the strap 224 of the implant 220 is disposed within the tissue. The needle 236 can be removed from the medical device 210 and the sleeve 226 is cut to remove the suture and sleeve from the implant strap 224, leaving the strap 224 within the tissue. The strap 224 can include a tanged portion (as discussed above) to self-affix to the tissue. This procedure can then be repeated for other dilator assemblies coupled to other straps of the implant 220 as needed. Each strap of the implant is pulled through a selected tissue site and the straps are adjusted to position and tension the implant.

As discussed above, over tensioning of the strap and/or suture during such a procedure can cause breakage of the suture and/or the strap and/or the medical device 210. To maintain the desired tension in the suture and/or dilator during such a procedure, an adaptor 200 (shown in FIGS. 4-6) can be coupled to the medical device 210 and used during the medical procedure. The below description of the use of an adaptor 200 is described with reference to the example medical device 210 and implant 220. It should be understood, however, that the adaptor 200 can be used with other types of medical devices and/or other implants.

The adaptor 200 can be constructed the same and function in a similar manner as described above for adaptor 100. In this embodiment, the adaptor 200 includes a body 208. The body 208 includes a first suture mounting portion 242 and a second suture mounting portion 244, a dilator holding portion 204, and a coupling portion 202 to couple the adaptor 200 to the medial device 210. The body 208 of the adaptor 200 can have a thickness TH and a length L as shown in FIG. 6. In one embodiment, the thickness TH is equal to about 0.40 in. and the length L is equal to about 0.85 in.

The suture mounting portion 242 defines a suture slit 250 and includes a radiused suture lead-in portion 254. The suture mounting portion 244 defines a suture slit 252 and includes a radiused suture lead-in portion 256. The suture mounting portions 242 and 244 can function in the same manner as described above for adaptor 100. For example, a portion of a suture (coupled to a suturing device, such as medical device 210) to be secured to tissue or to be used to secure an implant to tissue can be placed within the suture slit 250 or 252. The adaptor 200 can apply sufficient compression and/or friction force to the suture to maintain a tension on the suture during the medical procedure.

The dilator holding portion 204 includes a first lumen 246 for receiving a dilator, such as dilator 240, and the coupling portion 202 includes a second lumen 248 for receiving a medical device such as medical device 210. The first lumen 246 (also referred to as the "dilator lumen") extends through the body 208 between a front surface 258 and a rear surface 260 and is in fluid communication with an opening 241 defined in the front surface 258 and an opening (not shown) defined in the rear surface 260. As shown in FIGS. 4 and 5, the body 208 can include in the front surface 258, a chamfered or radiused edge 247 leading into the first lumen 246. Although not shown, the rear surface 260 can also include such a chamfered surface. The leading edge 247 can help ease the insertion of the dilator if, for example, the dilator is inserted into the lumen 246 via either the opening 241 in the front surface or the opening in the rear surface of the adaptor 200. The first lumen 246 is sized such that the adaptor 200 can apply a compression force on a dilator, producing a frictional force to maintain the dilator within the dilator lumen 246 as previously described for adaptor 100. In one embodiment, the dilator lumen 246 can have a diameter for example, of about 0.10 in. The dilator lumen 246 can have an inner perimeter or diameter that is slightly smaller than a diameter of the dilator 240.

In this embodiment, the body 208 of the adaptor 200 also defines a dilator slot 262 in fluid communication with the dilator lumen 246. The dilator slot 262 is defined by a first portion 264 and a second portion 266 that are deformable such that a dilator (e.g., dilator 240 shown in FIG. 3) can be moved through the slot 262 and positioned within the dilator lumen 246. The first portion 264 and second portion 266 are each radiused or chamfered to provide a lead-in to the slot 262 and provide ease of insertion of the dilator. For example, as a dilator is inserted in the direction of arrow M (see FIG. 4) the first portion 264 and second portion 266 will deform or move in the direction of arrows N and P, respectively. When the dilator is placed in the dilator lumen 246, the elastic material of the adaptor 200 allows the adaptor 200 to recover in an opposite direction of arrows N and P. The adaptor 200 compresses against the dilator to provide a friction and/or compression force on the dilator sufficient to maintain some tension applied to the dilator assembly (e.g., dilator assembly 222) by the user, and holds the dilator in the dilator lumen 246. The surface friction/compression can be overcome by the actuation of the medical device (e.g., medical device 210) to allow the dilator 240 to move in the direction of arrow R.

The second lumen 248 (also referred to as the medical device lumen) extends through the body 208 between a front surface 258 and a rear surface 260 and is in fluid communication with an opening 243 defined in the front surface 258 and an opening 245 (see FIG. 4) defined in the rear surface 260. As shown in FIGS. 4 and 5, the body 208 can include on the front surface 258 a chamfered or radiused edge 249 leading into the second lumen 248 to ease the insertion of a medical device (e.g., medical device 210) into the second lumen 248. Although not visible in the figures, the rear surface 260 can also include such a chamfered or radiused leading edge. The diameter D (see FIG. 5) of the lumen 248 can be slightly smaller than a diameter or outer perimeter of the medical device 210 such that the inner walls of the adaptor 200 that define the lumen 248 can maintain the position of the medical device (e.g., with friction forces) and also allow the user to adjust the position of the medical device 210 relative to the adaptor 200. In one embodiment, the diameter D of the lumen 248 can be, for example, about 0.39 in.

FIGS. 7 and 8 are a side view and top view, respectively, illustrating the adaptor 200 coupled to the medical device 210 (described above and illustrated in FIG. 2) and also coupled to the dilator assembly 222 (described above and illustrated in FIG. 3). To couple the adaptor 200 to the medical device 210, the shaft 212 of the medical device 210 can be inserted into the second lumen 248 of the adaptor 200. The adaptor 200 can be positioned at a desired location on the shaft 212 by rotating the adaptor 200 about an axis of the shaft 212 in the direction of arrows C or D and/or moving the adaptor 200 along a length of the shaft 212 in the direction of arrows A or B, as shown in FIG. 7. The walls of the body 208 that define the second lumen 248 secure the adaptor 200 to the shaft 212 with compression and/or friction force as described above.

With the adaptor 200 coupled to the medical device 210, the needle 236 of the dilator assembly 222 can be placed within the carrier 218 of the medical device 210 as described previously. The needle 236 can be coupled to the carrier 218 before or after the dilator 240 is coupled to the adaptor 200. The dilator 240 of the dilator assembly 222 can be moved or pushed through the dilator slot 262 and into the dilator lumen 246. As described above, the first portion 264 and the second portion 266 of the body 208 can deform such that the slot 262 is moved from a first width W1 (see FIG. 9a) to a second larger width W2 (see FIG. 9b) to allow the dilator 240 to pass through. After the dilator 240 is positioned within the dilator lumen 246, the first portion 264 and the second portion 266 can recover back to a relaxed state with the slot 262 returned to its first smaller width W1 (or substantially the size of the first width W1). In one example, the dilator slot 262 can be positioned at a 12 o'clock position (top of medical device 210 as shown in FIGS. 7 and 8) and about two inches from the handle 214 of the medical device 210.

With the needle 236 in the carrier 218 of the medical device 210 and the dilator 240 coupled to the adaptor 200, the dilator 240 can be pulled in the direction of arrow A to provide tension against the needle 236 such that the needle 236 is maintained in the carrier 218 and resist movement prior to activation of the medical device 210. The adaptor 200 will maintain the tension on the needle 236 (and suture 230) equal to, or substantially equal to, the friction force that the adaptor 200 can maintain. For example, the adaptor 200 can maintain about 1 pound-force or less of friction force on the dilator 240 (and therefore suture 230 and needle 236), which is below the typical level that can cause breakage or damage.

In use, the carrier 218 of the medical device 210 is positioned at a desired location within a patient (e.g., within a pelvic region), and the medical device 210 is actuated. As described above, during actuation, the actuator 216 is depressed or pushed to advance the carrier 218 in a circular path, which also advances the suture 230 and dilator 240 coupled thereto. The needle 236 is captured in the catch 228 of the medical device 210. The adaptor 200 maintains the tension on the suture 230 and needle 236 until actuation of the medical device 210, which is sufficient to overcome the compression and/or friction force of the adaptor 200.

Figure 10:
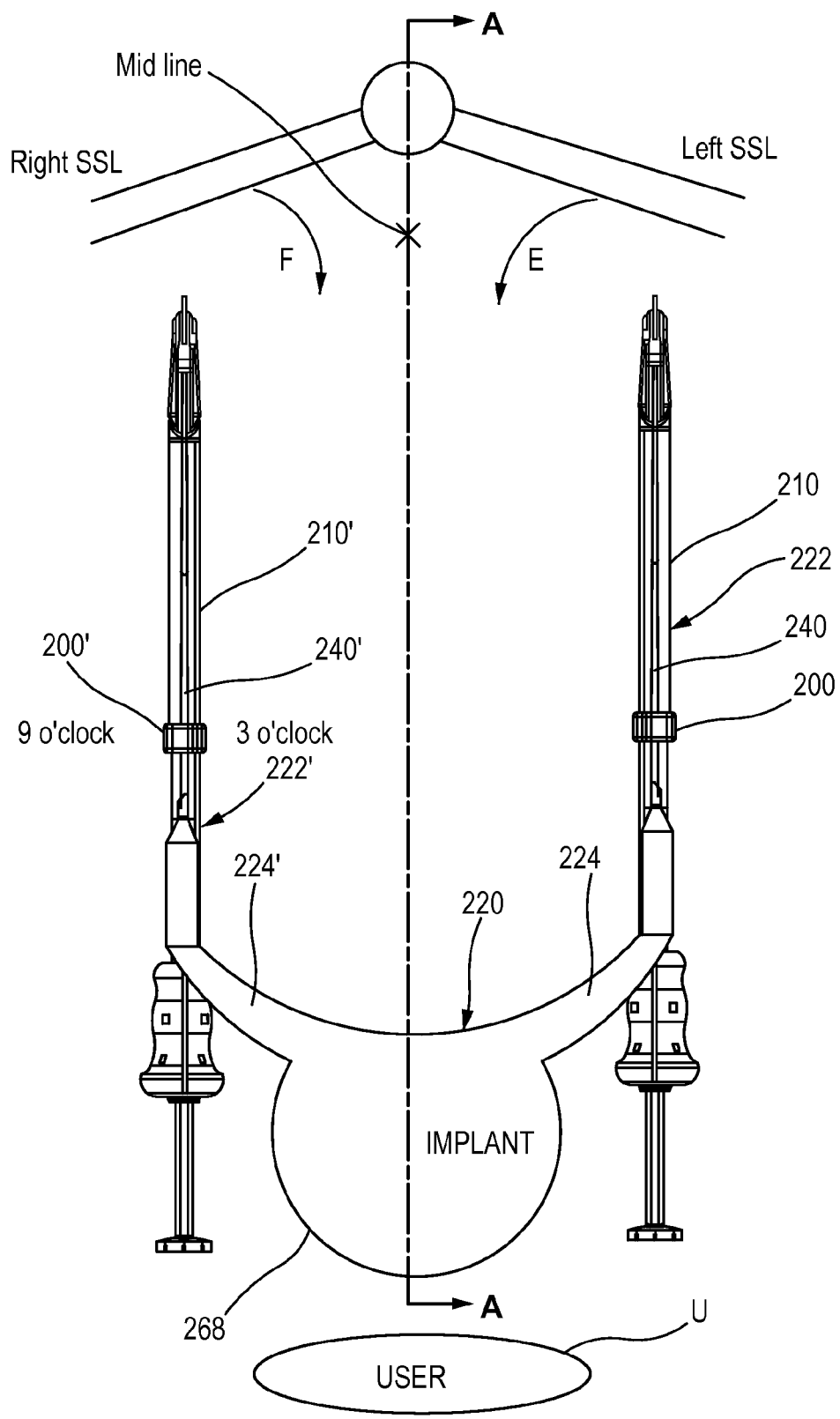
FIG. 10 is a top view illustrating two adaptors according to an embodiment, each coupled to a medical device and to a dilator assembly.

FIG. 10 illustrates the use of the adaptor 200 to prevent locking of the straps of an implant during an implantation procedure. Locking occurs when a strap of the implant becomes trapped between tissue (e.g., a sacrospinous ligament) and the body of the implant. The strap can become stuck or jammed against a body portion of the implant, which may make it difficult to maneuver or position the implant. FIG. 10 illustrates medical device 210 and a second medical device 210' (constructed the same as medical device 210), each with a dilator assembly 222, 222' and strap 224, 224' of an implant 220 coupled thereto. The implant 220 also includes a body portion 268 as shown. An adaptor 200 and an adaptor 200' are shown coupled to the medical devices 210 and 210', respectively. The dilator assembly 222' can be constructed the same as the dilator assembly 222 and the adaptor 200' can be constructed the same as the adaptor 200.

Figure 11:
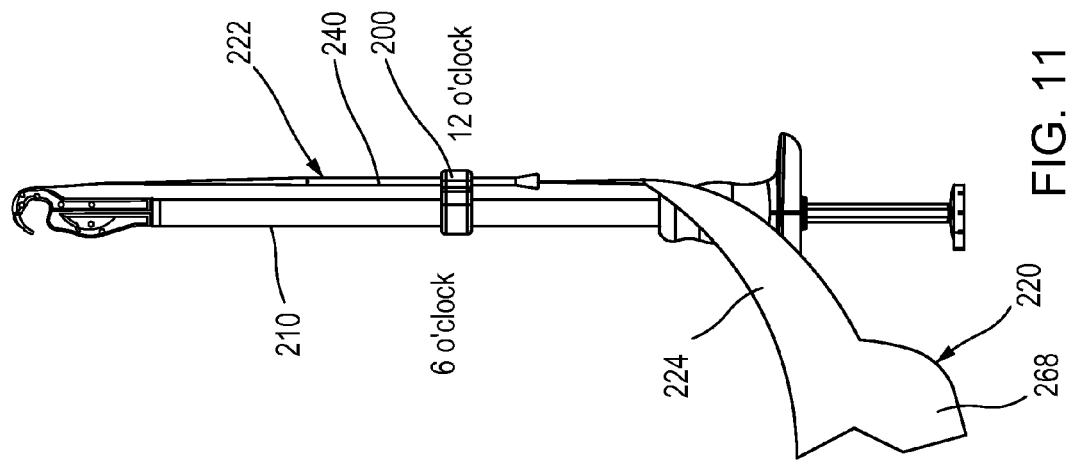
FIG. 11 is a side view taken along line A-A in FIG. 10.

In FIG. 10 the medical devices 210, 210' are shown in a top view as viewed by a user U standing and facing the patient. Medical devices 210, 210' are shown with the dilator slot (e.g., 262) of each adaptor 200, 200' shown in a 12 o'clock orientation (see also the side view of FIG. 11). In this example, the medical device 210 can be used to place the strap 224 of the implant 220 into a patient's left sacrospinous ligament (SSL) and the medical device 210' can be used to place the strap 224' into the patient's right SSL. FIG. 11 shows the orientation and positioning of the implant 220 relative to the medical device 210. The implant strap 224 and the body portion 268 of the implant 220 are positioned or directed from the 12 o'clock to a 9 o'clock position (e.g., toward a midline or medial area). In this orientation, after the medical device 210 has been actuated to pass the needle 236 through the left SSL and the needle 236 is in the catch 228 of the medical device 210 (as described above), the dilator 240 and the strap 224 (coupled thereto) can be pulled through the left SSL (see arrow E) and will follow the medical device 210 underneath the implant body portion 268 and avoid locking.

The orientation and positioning of the strap 224' relative to the medical device 210' shown in the top view of FIG. 10 is a mirror image of the orientation and position of the strap 224. The dilator slot of the adaptor 200' is positioned in a 12 o'clock position and the strap 224' and body portion 268 are directed towards a midline or medial from the 12 o'clock to a 3 o'clock position. In this orientation, when the dilator 240' is pulled through the patient's right SSL (see arrow F), the dilator 240' and strap 224' will follow the medical device 210' underneath the implant body portion 268 and avoid locking.

Figure 12:
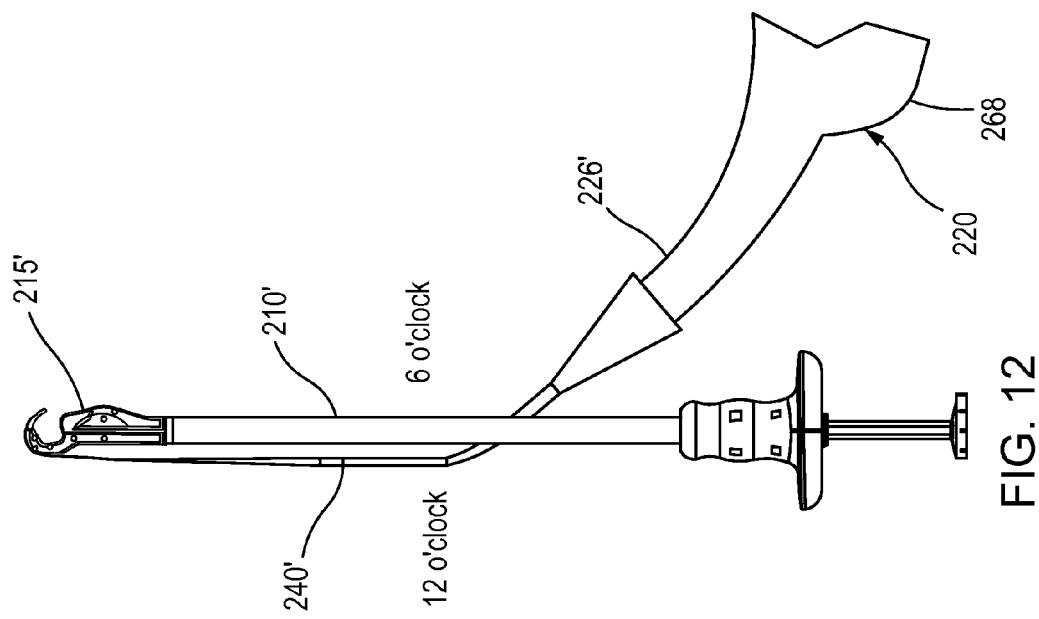
FIG. 12 is a side view illustrating an alternative orientation of a medical device of FIG. 10.

FIG. 12 is a side view illustrating an example of an undesirable positioning/orientation of the implant 220 relative to the medical device 210' without the use of an adaptor (e.g., adaptor 200'). The dilator 240' is shown wrapped around the shaft of the medical device 210' from a 12 o'clock to 9 o'clock to 6 o'clock position. In this orientation, when the dilator 240' is placed through the right SSL and the needle 236 is caught in the catch of the medical device 210', the dilator 240' will be pulled between the SSL and the body portion 268 of the implant 220, which can cause locking of the strap 224'. Although not shown, a mirror image of the above orientation applied to the strap 224 and dilator 240 can also result in the strap 224 to lock when placing the dilator 240 into the right SSL.

Although not visible in FIG. 12, the distal portion of the suture 230' can also, or alternatively, be wrapped about the head portion 215' of the medical device 210'. With the use of an adaptor 200', the dilator can be aligned and organized to the 12 o'clock position away from the immediate working field and the orientation can be clearly and correctly discerned to prevent locking.

The above example method of delivering and implanting straps of an implant is only one example use of the adaptor 200. The adaptor can also be used in a suturing procedure that does not include the use of a dilator. For example, in some procedures, an implant is sutured to a tissue, rather than being self-affixing. In such a procedure an adaptor 200 can be used with a medical device to deliver the strap of an implant in a procedure similar to as described above, and then the medical device can be reloaded with a needle coupled to a suture to be used to suture the strap in place. The user can load the needle into the carrier of the medical device as described above and place a portion of the suture within one of the suture mounting portions 242 or 244. The tension on the suture and needle can be maintained during the procedure as described above. In some procedures, a suture is used by itself to repair a tissue or support a portion of tissue, or to secure an implant, a stent or other implantable medical device within the body of a patient. The adaptor 200 can be used with a medical device to deliver and secure sutures in such procedures.

FIGS. 13-15 illustrate another embodiment of an adaptor 300. The adaptor 300 includes a body 308, a dilator holding portion 304 that includes a first lumen 346 for receiving a dilator, such as dilator 240, and a coupling portion 302 that includes a second lumen 348 for receiving a medical device, such as medical device 210.

The first lumen 346 (also referred to as the "dilator lumen") extends through the body 308 between a front surface 358 and a rear surface 360 and is in fluid communication with an opening 341 defined in the front surface 358 and an opening (not shown) defined in the rear surface 360. Similarly, the second lumen 348 (also referred to as the medical device lumen) extends through the body 308 between the front surface 358 and the rear surface 360 and is fluid communication with an opening 343 defined in the front surface 358 and an opening 345 defined in the rear surface 360. The body 308 also defines a dilator slot 362 in fluid communication with the dilator lumen 346. The dilator slot 362 is defined by a first portion 364 and a second portion 366 that are deformable such that a dilator (e.g., dilator 240) can be moved through the slot 362 and positioned within the dilator lumen 346 as described above for previous embodiments. The first portion 364 and second portion 366 can each be radiused or chamfered and define a lead-in region 365 to provide ease of insertion of the dilator into the slot 362.

In this embodiment, the lead-in region 365 also serves as a suture mounting portion. As shown in FIGS. 13 and 14, a suture slit 350 is defined in the body 308 and in fluid communication with the dilator lumen 346. A portion of a suture can be placed and held within the suture slit 350 in a similar manner as described above for previous embodiments.

In this embodiment, the body 308 also defines a slot 370 in fluid communication with the second lumen 348. The slot 370 is defined by a first portion 372 and a second portion 374 of the body 308. The first portion 372 and the second portion 374 are deformable such that a medical device (e.g., medical device 210) can be moved through the slot 370 and positioned within the second lumen 348. The elastic or resilient material of the adaptor 300 allows the first portion 372 and the second portion 374 to move apart to allow a medical device to move through the slot 370 and into the lumen 348. The first portion 372 and the second portion 374 can recover back to their original position after the medical device is disposed within the lumen 348. Thus, similar to the slot 262 described above, the slot 372 can have a first width that is sufficiently small to maintain the medical device within the lumen 348. When the first portion 372 and the second portion 374 deform or spread apart, the slot 370 has a larger width sufficient to allow the medical device to pass therethrough. Although not shown, the first portion 372 and the second portion 374 can each be radiused or chamfered to provide a lead-in region to the slot 370 and provide ease of insertion of a medical device.

The adaptor 300 can function in a similar manner and be used in a similar manner as described above for previous embodiments. In use, a medical device (e.g., medical device 210) can be moved through the slot 370 and placed in the second lumen 348 and a dilator can be placed through the lead-in region 365 and moved through the slot 362 and into the first lumen 346. Alternatively, a suture can be inserted through the dilator lead-in region 365, through the dilator lumen 346 and placed within the suture slit 350. As described above for adaptor 200, the adaptor 300 can maintain the tension on a suture and needle until actuation of the medical device (e.g., medical device 210) overcomes the friction force of the adaptor 300.

FIGS. 16-18 illustrate another embodiment of an adaptor. An adaptor 400 can be constructed the same and function in a similar manner as described above for previous embodiments. In this embodiment, the adaptor 400 includes a body 408 that has a narrower thickness TH than, for example, the adaptor 200. The body 408 of the adaptor 400 can have a thickness TH and a length L as shown in FIG. 18. In one embodiment, the thickness TH is equal to about 0.15 in. and the length L is equal to about 0.89 in. The body 408 includes a first suture mounting portion 442 and a second suture mounting portion 444, a dilator holding portion 404, and a coupling portion 402 to couple the adaptor 400 to a medical device, such as medical device 210. The suture mounting portion 442 defines a suture slit 450 and includes a radiused suture lead-in portion 454. The suture mounting portion 444 defines a suture slit 452 and includes a radiused suture lead-in portion 456. The suture mounting portions 442 and 444 can function in the same manner as described above for previous embodiments.

The dilator holding portion 404 includes a first lumen 446 for receiving a dilator, such as dilator 240, and the coupling portion 402 includes a second lumen 448 for receiving a medical device such as medical device 210. The first lumen 446 (also referred to as the "dilator lumen") extends through the body 408 between a front surface 458 and a rear surface 460 and is in fluid communication with an opening 441 defined in the front surface 458 and an opening (not shown) defined in the rear surface 460. The body 408 can optionally include in the front surface 458 a chamfered or radiused edge (not shown) leading into the first lumen 446, and the rear surface 460 can also include such a chamfered surface as discussed above with reference to adaptor 200 and adaptor 300. The first lumen 446 is sized such that the adaptor 400 can apply a compression force on a dilator, producing a frictional force to maintain the dilator within the dilator lumen 446 as previously described.

The body 408 of the adaptor 400 also defines a dilator slot 462 in fluid communication with the dilator lumen 446. The dilator slot 462 is defined by a first portion 464 and a second portion 466 that are deformable such that a dilator (e.g., dilator 240) can be moved through the slot 462 and positioned within the dilator lumen 446. The first portion 464 and second portion 466 are each radiused or chamfered to provide a lead-in region to the slot 462 and provide ease of insertion of the dilator as described above for adaptor 200 and adaptor 300.

The second lumen 448 (also referred to as the medical device lumen) extends through the body 408 between the front surface 458 and the rear surface 460 and is in fluid communication with an opening 443 defined in the front surface 458 and an opening 445 (see FIG. 16) defined in the rear surface 460. The body 408 can optionally include on the front surface 458 a chamfered or radiused edge (not shown) leading into the second lumen 448 to ease the insertion of a medical device (e.g., medical device 210) into the second lumen 448 and the rear surface 460 can also include such a chamfered or radiused leading edge. The diameter D (see FIG. 17) of the lumen 448 can be slightly smaller than a diameter or outer perimeter of a medical device (e.g., medical device 210) as previously described. In one embodiment, the diameter D of the lumen 448 can be, for example, about 0.37 in.

The adaptor 400 can function in a similar manner and be used in a similar manner as described above for previous embodiments. In use, a medical device (e.g., medical device 210) can be placed in the second lumen 448 and a dilator can be placed in the first lumen 446 as described above for adaptor 200. A portion of a suture can be placed and held within the suture slit 450 and/or the suture slit 452 in a similar manner as described above for previous embodiments. The adaptor 400 can maintain the tension on a suture and needle until actuation of the medical device (e.g., medical device 210) overcomes the friction force of the adaptor 400.

Figure 19:
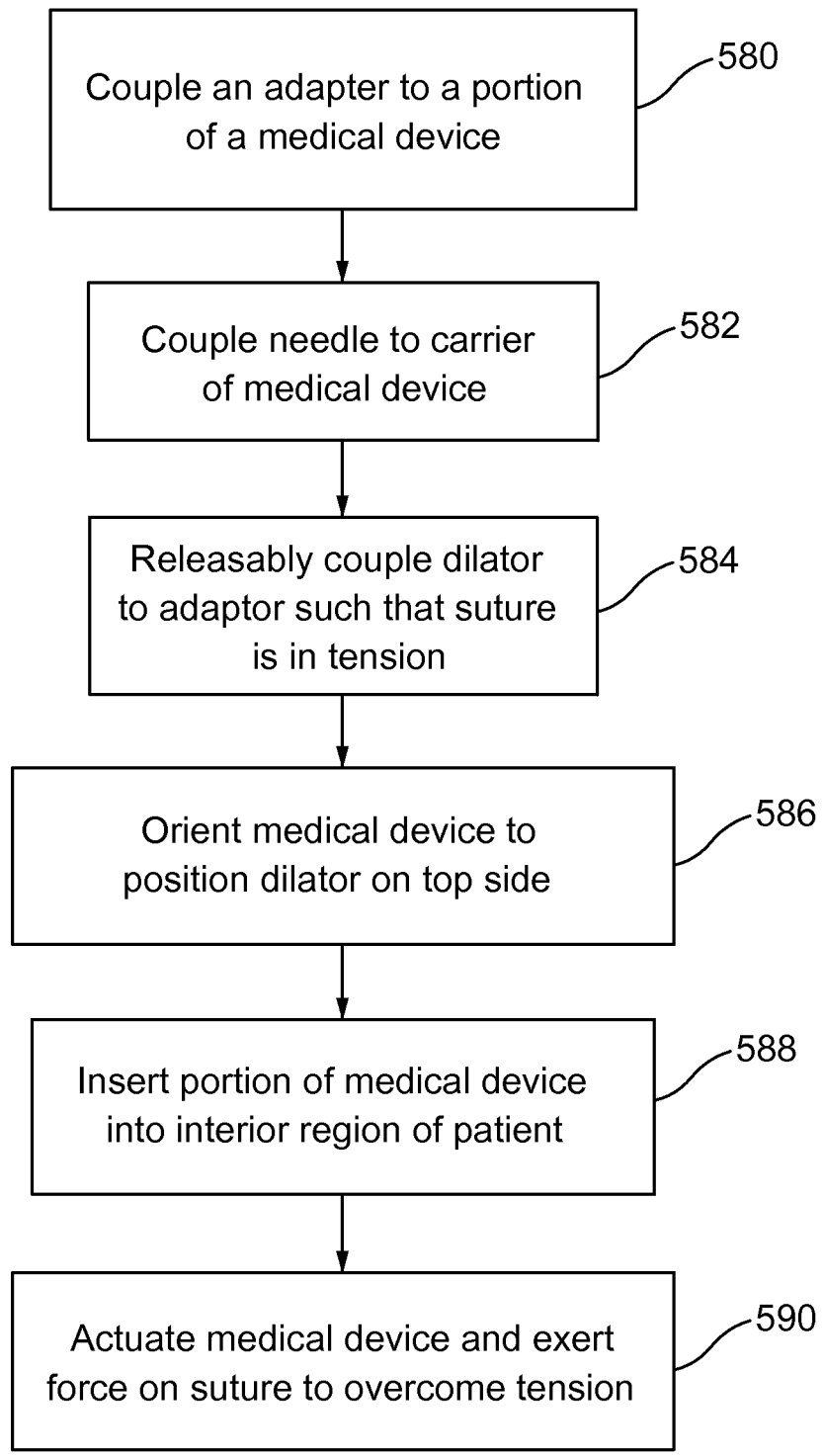
FIGS. 19 and 20 are each a flow chart illustrating a method of using an adaptor in a medical procedure according to different embodiments.

FIG. 19 is a flow chart illustrating a method of using a medical device and adaptor to perform a procedure to deliver and secure an implant according to one embodiment. At 580, an adaptor is coupled to a portion of a medical device as described herein. At 582, a needle within a carrier of the medical device is coupled to the medical device. The needle can be coupled to a suture and the suture can be coupled to a dilator as described herein. At 584, the dilator can be releasably coupling the adaptor such that the adaptor exerts a friction force on the dilator sufficient to maintain tension on the suture in a first direction. At 586, the medical device can be oriented such that the dilator is positioned on a top side of the medical device and the strap of the implant extends from the dilator toward a midline. At 588, at least a portion of the medical device is inserted into an interior region of a patient to perform a medical procedure. At 590, the medical device is actuated such that the medical device exerts a force on the suture in a second direction opposite the first direction sufficient to overcome the tension on the suture by the adaptor.

Figure 20:
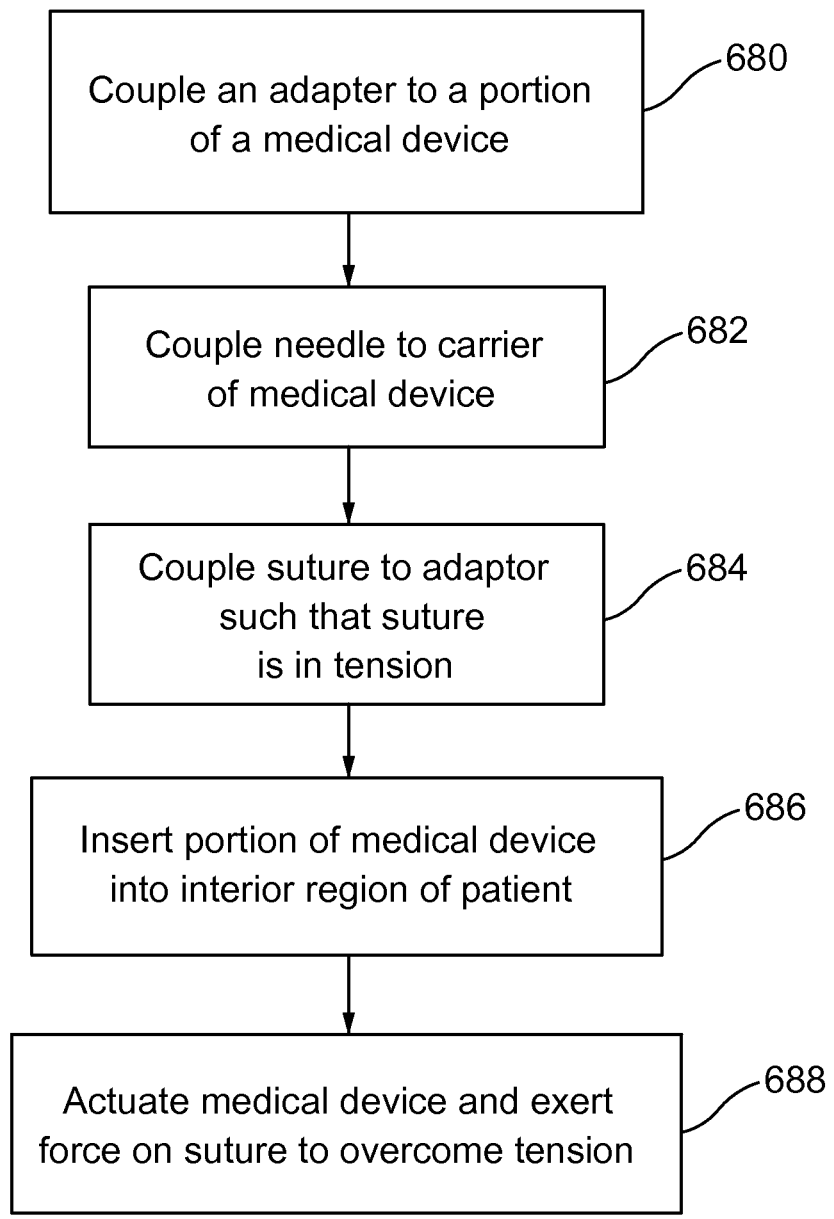

FIG. 20 is a flow chart illustrating a method of using a medical device and adaptor to perform a suturing procedure according to one embodiment. At 680, an adaptor is coupled to a portion of a medical device as described herein. At 682, a needle coupled to a suture is coupled to the medical device. For example, the needle is placed within a carrier of the medical device as described above. At 684, a portion of the suture is placed within a suture mounting portion of the adaptor. For example, the suture can be placed within a suture slit configured to exert a friction force on the suture to maintain tension on the suture in a first direction. At 686, at least a portion of the medical device is inserted into an interior region of a patient to perform a medical procedure. At 688, the medical device is actuated such that the medical device exerts a force on the suture in a second direction opposite the first direction sufficient to overcome the tension on the suture by the adaptor.

Figure 21:
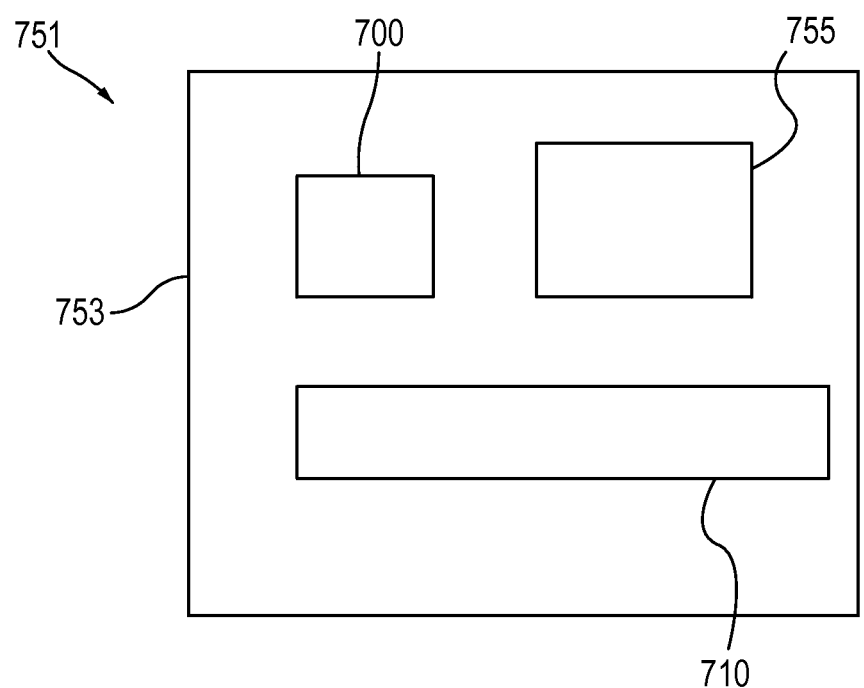
FIG. 21 illustrates a kit according to an embodiment.

FIG. 21 is a schematic illustration of a kit according to an embodiment. As shown in FIG. 21, a kit 751 can include at least one adaptor 700 and at least one medical device 710 as described herein. The adaptor 700 and medical device 710 can be provided together in a container 753. The container 753 can be any type of container or package in which the components of the kit 700 can be placed and provided to a user. For example, the container 753 can be a case, a pouch, an envelope, a box, a bag, etc. The kit 700 can also include assembly instructions 755 for assembling or coupling together the adaptor 700 and the medical device 710. In some embodiments, a kit 751 can also include suture, needles and/or other components used in a suturing procedure. In some embodiments, a kit 751 can also include an implant and dilator assembly as described herein.

In one embodiment, an apparatus to aid in the placement of a suture at a location within a body of a patient using a medical device includes a body and a coupler configured to couple the body to the medical device. The apparatus further includes a suture mounting portion disposed on the body that defines a suture slit configured to laterally receive therethrough a portion of a suture coupled to the medical device and to apply a frictional force to the suture to resist movement of the suture longitudinally therethrough. A magnitude of the frictional force being less than a longitudinal force applied to the suture by actuation of the medical device.

In such an embodiment, at least one of the coupler or the suture mounting portion is formed with an elastic material. In some embodiments, the coupler includes a lumen defined by the adaptor and extending between an opening defined in a front surface of the coupler and an opening defined in a back surface of the coupler. The lumen can be configured to receive a shaft of a medical device therethrough. In some embodiments, the coupler defines a slot in communication with the lumen, and the slot can deform between a first width in which a shaft of a medical device can be moved through the slot and into the lumen and a second width that is smaller than an outer perimeter of the shaft of the medical device such that the medical device is maintained within the lumen. In some embodiments, the suture mounting portion is configured to exert a frictional force on the portion of the suture within the suture slit of less than 1 pound-force. In some embodiments, the suture mounting portion is a first suture mounting portion and the suture slit is a first suture slit, and the apparatus further includes a second suture mounting portion that defines a second suture slit. The second suture slit can be configured to receive therethrough a portion of a suture coupled to a medical device. In some embodiments, the apparatus further includes a dilator holding portion configured to releasably couple a dilator to the medical device and the adaptor is configured to maintain a tension on a suture coupled to the dilator substantially equal to a force exerted by the adaptor on the dilator.

In another embodiment, an apparatus includes an adaptor couplable to a medical device. The adaptor is configured to assist in the delivery of a suture or an implant being placed inside a body of a patient with the medical device. The adaptor defines a dilator holding portion configured to releasably couple a dilator to the adaptor, the dilator being couplable to the medical device. The adaptor is configured to maintain a tension on a portion of a suture coupled to the dilator substantially equal to a force exerted by the adaptor on the dilator.

In such an embodiment, the adaptor can be formed with an elastic material. In some embodiments, the dilator holding portion can include a lumen defined by the adaptor that extends between an opening defined in a front surface of the adaptor and an opening defined in a back surface of the adaptor. The lumen can be configured to receive therethrough a portion of a dilator. In some embodiments, the adaptor further defines a slot in communication with the lumen and the adaptor is configured to deform between a first width in which a dilator can be moved through the slot and into the lumen, and a second that is smaller than an outer perimeter of the dilator such that the dilator is maintained within the lumen. In some embodiments, the adaptor defines a lumen extending between an opening defined in a front surface of the adaptor and an opening defined in a back surface of the adaptor, and the lumen can be configured to receive a portion of a medical device therethrough. In some embodiments, the adaptor further defines a slot in communication with the lumen and the adaptor is configured to deform such that the slot has a first width in which a shaft of a medical device can be moved through the slot and into the lumen and the slot has a second width smaller than an outer perimeter of the shaft of the medical device such that the medical device is maintained within the lumen. In some embodiments, the adaptor is configured to maintain a tension on the suture coupled to the dilator. In some embodiments, the adaptor is configured to exert a force on the dilator of less than 1 pound-force to maintain a tension on the suture coupled to the dilator.

In another embodiment, a method includes coupling an adaptor to a portion of a medical device. A needle is coupled within a carrier of the medical device. The needle being coupled to a suture and the suture being coupled to a dilator. The dilator is releasably coupled to the adaptor such that the adaptor exerts a force on the dilator sufficient to maintain tension on the suture in a first direction. At least a portion of the medical device is inserted into an interior region of a patient to perform a medical procedure.

In such an embodiment, the method can also include actuating the medical device such that a force is exerted on the suture in a second direction opposite the first direction sufficient to overcome the tension on the suture by the adaptor. In some embodiments, coupling the adaptor includes inserting the shaft of the medical device into a lumen defined by the adaptor. In some embodiments, the adaptor defines a slot in communication with the lumen, and coupling the adaptor includes inserting the shaft of the medical device through the slot and into the lumen. In some embodiments, releasably coupling the dilator includes inserting the dilator through a lumen defined by the adaptor. In some embodiments, the adaptor defines a slot in communication with the lumen, and releasably coupling the dilator includes inserting the dilator through the slot and into the lumen. In some embodiments, the dilator is coupled to a strap of an implant, and prior to inserting at least a portion of the medical device, the medical device is oriented such that the dilator is positioned on a top side of the medical device and the strap of the implant extends from the dilator toward a midline.

In another embodiment, an apparatus includes a medical device configured to place a suture in a body of a patient and an adaptor couplable to the medical device. The adaptor is configured to assist in the delivery of a suture being placed inside a body of a patient with the medical device. The adaptor is configured to maintain a tension on a portion of the suture coupled to the medical device.

In such an embodiment, the adaptor can include a suture mounting portion that defines a suture slit configured to receive laterally therethrough a portion of a suture coupled to the medical device. The suture slit can apply a force to the suture to resist movement of the suture longitudinally therethrough. A magnitude of the force can be less than a longitudinal force applied to the suture by actuation of the medical device. In some embodiments, the adaptor includes a dilator holding portion configured to releasably couple a dilator to the adaptor. The dilator can be coupled to a portion of a suture and the suture can be couplable to the medical device. In such an embodiment, the adaptor can maintain a tension on a portion of the suture coupled to the medical device substantially equal to a force exerted by the adaptor on the dilator. In some embodiments, the dilator holding portion defines a lumen and a slot in communication with the lumen and a dilator is configured to be inserted through the slot and into the lumen. In some embodiments, the adaptor includes a lumen and the medical device is configured to be slidably received through the lumen to couple the adaptor to the medical device. In such an embodiment, the adaptor can include a slot in communication with the lumen, and the medical device is configured to be moved through the slot and into the lumen. In some embodiments, the apparatus can include instructions for assembly of the medical device and the adaptor.

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, an adaptor (e.g., 100, 200, 300, 400, 700) can include various combinations and/or sub-combinations of any of the components and/or features of the different embodiments described herein. For example, any of the embodiments of an adaptor can include one or more suture mounting portions and/or one or more dilator holders. Thus, an adaptor can be configured to be used with more than one dilator assembly at a time. In some embodiments, an adaptor may only include one or more suture mounting portions and no dilator holder. In some embodiments, an adaptor may include only one or more dilator holders and no suture mounting portions.

Although the adaptors (100, 200, 300, 400, 700) were shown and described being used with specific embodiments of a medical device (110, 210, 710), an adaptor can be configured for use with other types of medical devices, including other types of suturing and/or delivery devices. In some embodiments, more than one adaptor can be used with a single medical device (e.g., 110, 210, 710). An adaptor can be configured to be used with other types of dilator assemblies than the dilator assemblies descried herein. An adaptor can also be configured to hold a different portion of a dilator assembly, for example, a sleeve of a dilator assembly rather than the dilator portion. An adaptor can have a variety of different shapes and sizes. For example, an adaptor can have a different length, width, outer perimeter, lumen sizes, etc.

The adaptors and medical devices described herein can be used to perform various types of medical procedures at various locations within a patient's body. The adaptors and medical devices can be used to during various suturing procedures and procedures to suture and/or secure various types of stents and implants within a patient's body, including for example, implants for pelvic floor applications and stents such as, for example, TB, duodenal, esophageal stents, biliary or colonic stents.

What is claimed is:

1. An apparatus to aid in the placement of a suture at a location within a body of a patient using a medical device, comprising:
a suture;
a dilator;
a medical device having a shaft;
a coupler configured to couple to a portion of the medical device;
a suture mounting portion disposed on the coupler and defining a suture slit configured to receive laterally therethrough a portion of the suture coupled to the medical device and to apply a frictional force to the suture to resist movement of the suture longitudinally therethrough, a magnitude of the frictional force being less than a longitudinal force applied to the suture by actuation of the medical device;
a dilator mounting portion disposed on the coupler and configured to releasably couple the dilator to the coupler and to apply a frictional force to the dilator to resist movement of the dilator longitudinally therethrough, the dilator mounting portion being disposed apart from the suture mounting portion, the dilator mounting portion including a first lumen defined by the coupler and extending between a first opening defined by a front surface of the coupler and a second opening defined by a back surface of the coupler, the first lumen being configured to receive therethrough a portion of the dilator, the first lumen having a size larger than a size of the suture slit of the suture mounting portion; and
a medical device mounting portion disposed on the coupler and configured to releasably couple the shaft of the medical device to the coupler, the medical device mounting portion including a second lumen extending between a third opening defined by the front surface and a fourth opening defined by the back surface, the second lumen being configured to receive therethrough a portion of the shaft of the medical device, the second lumen extending in a same direction as the first lumen, the second lumen having a size larger than the size of the first lumen, the second lumen having a size larger than the size of the suture slit, the front surface of the coupler defining a portion extending completely around the third opening,
at least one of the suture mounting portion and the dilator mounting portion being formed of an elastic material.

2. The apparatus of claim 1, wherein the back surface of the coupler defines a portion extending completely around the fourth opening.

3. The apparatus of claim 1, wherein the suture mounting portion is configured to exert a frictional force on the portion of the suture within the suture slit of less than 1 pound-force.

4. The apparatus of claim 1, wherein the suture mounting portion is a first suture mounting portion and the suture slit is a first suture slit, and further comprising a second suture mounting portion defining a second suture slit, the second suture slit configured to receive therethrough a portion of a suture coupled to the medical device, the first lumen being disposed between the first suture slit and the second suture slit.

5. The apparatus of claim 1, wherein the dilator mounting portion is configured to maintain a tension on the suture coupled to the dilator substantially equal to the frictional force exerted by the dilator mounting portion on the dilator.

6. The apparatus of claim 1, wherein the portion extending completely around the third opening includes a chamfered portion.

7. An apparatus, comprising:
a medical device having a shaft, and a needle carrier;
a dilator having a needle configured to be coupled to the needle carrier; and
an adaptor configured to be coupled to the shaft of the medical device, the adaptor configured to assist in the delivery of a suture or an implant being placed inside a body of a patient with the medical device, wherein the adaptor is formed with an elastic material,
the adaptor defining a dilator holding portion, a suture mounting portion, and a medical device mounting portion, the dilator holding portion being disposed radially from the suture mounting portion, the dilator holding portion configured to releasably couple the needle of the dilator to the adaptor, the dilator holding portion including a first lumen defined by the adaptor and extending between a first opening defined by a front surface of the adaptor and a second opening defined by a back surface of the adaptor, the first lumen configured to receive therethrough a portion of the needle of the dilator,
the suture mounting portion defining a suture slit configured to receive a portion of the suture to releasably couple the suture to adaptor, the suture mounting portion configured to apply a frictional force to the suture to resist movement of the suture longitudinally through the suture slit, the first lumen of the dilator holding portion having a size greater than the size of the suture slit,
the medical device mounting portion being configured to releasably couple the shaft of the medical device to the adaptor, the medical device mounting portion including a second lumen defined by the adaptor, the second lumen being configured to receive therethrough a portion of the shaft of the medical device, the second lumen extending in a same direction as the first lumen, the second lumen being disposed adjacent to the first lumen along a longitudinal axis of the adaptor, the second lumen having a size larger than the size of the first lumen.

8. The apparatus of claim 7, wherein the adaptor further defines a slot in communication with the first lumen, the slot configured to deform between a first width in which the dilator can be moved through the slot and into the first lumen and a second width, the second width being smaller than an outer perimeter of the dilator such that the dilator is maintained within the first lumen, the slot being disposed at a location that intersects with the longitudinal axis of the adaptor.

9. The apparatus of claim 7, wherein the second lumen extends between a third opening defined by a front surface of the adaptor and a fourth opening defined by a back surface of the adaptor.

10. The apparatus of claim 7, wherein the adaptor is configured to maintain a tension on the suture coupled to the dilator.

11. The apparatus of claim 7, wherein the adaptor is configured to exert a force on the dilator of less than 1 pound-force to maintain a tension on the suture coupled to the dilator.

12. An apparatus, comprising:
a medical device having a shaft, and a needle carrier;
a dilator having a needle configured to be coupled to the needle carrier; and
a coupler configured to be coupled to the shaft of the medical device,
the coupler including a first mounting portion, a second mounting portion, and a third mounting portion, the first mounting portion including a suture slit in communication with an outer surface of the coupler and configured to receive a portion of a suture,
the second mounting portion including a first lumen defined by the coupler and a slot, the second mounting portion being separate from the first mounting portion, the first lumen extends from a front surface of the coupler to a back surface of the coupler, the slot extending from the first lumen to an outer surface of the coupler, the first lumen having a size that is greater than a size of the suture slit of the first mounting portion, the first lumen configured to receive a portion of the needle of the dilator,
at least one of the first mounting portion and the second mounting portion being formed of an elastic material,
the third mounting portion being configured to releasably couple the shaft of the medical device to the coupler, the third mounting portion including a second lumen defined by the coupler, the second lumen being configured to receive therethrough a portion of the shaft of the medical device, the second lumen extending in a same direction as the first lumen, the second lumen being disposed adjacent to the first lumen along a longitudinal axis of the coupler such that the first lumen and the second lumen intersect with the longitudinal axis of the coupler at different locations, the second lumen having a size larger than the size of the first lumen, the size of the second lumen being larger than the size of the suture slit.

13. The apparatus of claim 12, wherein the slot is in fluid communication with the first lumen such that the portion of the dilator may be moved through the slot and into the first lumen.

14. The apparatus of claim 12, wherein the coupler defines a chamfered or radiused portion disposed adjacent the slot.

15. The apparatus of claim 12, wherein the coupler defines an opening on the front surface of the coupler and an opening on the back surface of the coupler, the first lumen extending from the opening on the front surface to the opening on the back surface.

* * * * *

UNITED STATES PATENT AND TRADEMARK OFFICE
CERTIFICATE OF CORRECTION

PATENT NO. : 9,820,730 B2
APPLICATION NO. : 12/970381
DATED : November 21, 2017
INVENTOR(S) : Michael S. H. Chu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 967 days.

Signed and Sealed this

Twenty-fifth Day of September, 2018

Andrei Iancu
*Director of the United States Patent and Trademark Office*